(12) United States Patent
Terranova et al.

(10) Patent No.: US 6,306,181 B1
(45) Date of Patent: Oct. 23, 2001

(54) CATIONIC 4-HYDROXYINDOLES, THEIR USE FOR THE OXIDATION DYEING OF KERATINOUS FIBERS, DYEING COMPOSITIONS, AND METHODS OF DYEING

(75) Inventors: Eric Terranova, Bois Colombes; Aziz Fadli, Chelles; Alain Lagrange, Coupvray, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/400,818

(22) Filed: Sep. 21, 1999

(30) Foreign Application Priority Data

Sep. 21, 1998 (FR) .................................................. 98 11751

(51) Int. Cl.$^7$ ................................................. A61K 7/13
(52) U.S. Cl. ................ 8/409; 8/423; 8/426; 8/573; 8/568; 8/654; 8/655; 8/574; 8/606
(58) Field of Search ................ 8/409, 423, 426, 8/573, 568, 654, 655, 574, 606, 407; 548/490, 504, 312.1; 546/277.4; 564/281

(56) References Cited

U.S. PATENT DOCUMENTS

| | | | | |
|---|---|---|---|---|
| 3,228,959 | * | 1/1966 | Gyermek | 548/504 |
| 3,673,213 | * | 6/1972 | Zaffaroni | 548/504 |
| 3,732,249 | * | 5/1973 | Ishizaka | 548/504 |
| 4,600,776 | * | 7/1986 | Meisel et al. | 544/198 |
| 5,227,397 | * | 7/1993 | Saccomano et al. | 548/495 |
| 5,454,841 | * | 10/1995 | Wolfram et al. | 8/406 |
| 5,609,649 | | 3/1997 | Junino et al. | 8/409 |
| 5,702,712 | * | 12/1997 | Wenke et al. | 8/405 |
| 5,704,948 | | 1/1998 | Terranova et al. | 8/409 |
| 5,869,692 | | 2/1999 | Terranova et al. | 548/503 |

FOREIGN PATENT DOCUMENTS

| | | |
|---|---|---|
| 23 59 399 | 6/1975 | (DE) . |
| 38 43 892 | 6/1990 | (DE) . |
| 41 33 957 | 4/1993 | (DE) . |
| 195 43 988 | 5/1997 | (DE) . |
| 0 428 441 | 5/1991 | (EP) . |
| 0 446 131 | 9/1991 | (EP) . |
| 0 850 638 | 7/1998 | (EP) . |
| 2 733 749 | 11/1996 | (FR) . |
| 2 736 640 | 1/1997 | (FR) . |
| 2 750 048 | 12/1997 | (FR) . |
| 9-110659 | 4/1997 | (JP) . |
| WO 94/08969 | 4/1994 | (WO) . |
| WO 94/08970 | 4/1994 | (WO) . |
| 94/10968 | * 5/1994 | (WO) . |
| WO 96/15765 | 5/1996 | (WO) . |

OTHER PUBLICATIONS

CAPLUS Abstract of Jasys et al, "Novel Quaternary Ammonium Salt–Containing Polyamines from the *Agelenopsis aperta* Funnel Spider Web," J. Org. Chem. 57(6), 1814–20, (1992).*
CAPLUS Abstract of Quistad et al, "Structures of Paralytic Acylpolyamines from the spider *Agelenopsis aperta,*" Biochem. Biophys. Res. Commum. 169(1), 51–6, 1990.*
English language Derwent Abstract of DE 23 59 399, Jun. 1975.
English language Derwent Abstract of DE 38 43 892, Jun. 1990.
English language Derwent Abstract of DE 41 33 957, Apr. 1993.
English language Derwent Abstract of DE 195 43 988, May 1997.
English language Derwent Abstract of EP 0 446 131, Sep. 1991.
English language Derwent Abstract of EP 0 850 638, Jul. 1998.
English language Derwent Abstract of FR 2 733 749, Nov. 1996.
English language Derwent Abstract of FR 2 750 048, Dec. 1997.
English language Derwent Abstract of JP 2019576, Jan. 1990.
English language Derwent Abstract of JP 9–110659, Apr. 1997.

* cited by examiner

*Primary Examiner*—Margaret Einsmann
(74) *Attorney, Agent, or Firm*—Finnegan Henderson Farabow Garrett & Dunner, L.L.P.

(57) ABSTRACT

The invention relates to novel 4-hydroxyindole derivatives comprising at least one cationic group Z, Z being selected from quaternized aliphatic chains, aliphatic chains containing at least one quaternized saturated ring, and aliphatic chains containing at least one quaternized unsaturated ring, to their use as a coupler for the oxidation dyeing of keratinous fibers, to the dyeing compositions comprising them, and to the methods of oxidation dyeing which employ them.

56 Claims, No Drawings

CATIONIC 4-HYDROXYINDOLES, THEIR USE FOR THE OXIDATION DYEING OF KERATINOUS FIBERS, DYEING COMPOSITIONS, AND METHODS OF DYEING

The invention relates to novel 4-hydroxyindole derivatives comprising at least one cationic group Z, Z being selected from quaternized aliphatic chains, aliphatic chains containing at least one quaternized saturated ring, and aliphatic chains containing at least one quaternized unsaturated ring, to their use as a coupler for the oxidation dyeing of keratinous fibers, to the dyeing compositions comprising them, and to the methods of oxidation dyeing which employ them.

It is known to dye keratinous fibers, and especially human hair, with dyeing compositions comprising oxidation dye precursors, especially para-phenylenediamines, ortho- or para-aminophenols, and heterocyclic compounds, such as diaminopyrazole derivatives, which are referred to generally as oxidation bases. The oxidation dye precursors or oxidation bases are colourless or slightly coloured compounds which, when combined with oxidizing products, have the capacity to give rise to coloured compounds and dyes by virtue of a process of oxidative condensation.

It is also known that the shades obtained with these oxidation bases can be varied by combining them with couplers or coloration modifiers, the latter being selected in particular from aromatic meta-diamines, meta-aminophenols, meta-diphenols and certain heterocyclic compounds such as, for example, indole couplers.

The variety of molecules employed as oxidation bases and couplers makes it possible to obtain a wide range of colours.

The so-called permanent coloration obtained by virtue of these oxidation dyes should, moreover, satisfy certain conditions. Hence it should have no toxicological drawbacks, should allow shades of the desired intensity to be obtained, and should have good resistance to external agents (light, inclement weather, washing, permanent-waving, perspiration and friction).

The dyes should also allow white hair to be covered and, finally, they should be as unselective as possible; in other words, they should allow the smallest possible differences in coloration to be produced over the entire length of a single keratinous fibre, which may in fact be sensitized (i.e. damaged) differently between its tip and its root.

The inventors have now discovered, in a manner totally unexpected and surprising, that a novel class of 4-hydroxyindole derivatives of formula (I) defined below, containing at least one cationic group Z, Z being selected from quaternized aliphatic chains, aliphatic chains containing at least one quaternized saturated ring, and aliphatic chains containing at least one quaternized unsaturated ring, are suitable for use as a coupler for oxidation dyeing and that, furthermore, they make it possible to obtain dyeing compositions which lead to intense colorations in a very wide range of shades and have excellent properties of resistance to the various treatments which the keratinous fibers may undergo. Finally, these compounds have been found to be readily synthesizable.

It is these discoveries which form the basis of the present invention.

The invention therefore provides, firstly, 4-hydroxyindole derivatives of formula (I) below and their addition salts with an acid:

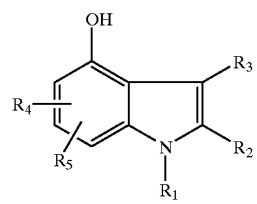

(I)

in which:

$R_1$ represents a hydrogen atom; a group Z; a $C_1$–$C_4$ alkyl radical; a $C_1$–$C_4$ monohydroxyalkyl radical; a $C_2$–$C_4$ polyhydroxyalkyl radical; a ($C_1$–$C_4$ alkoxy)-$C_1$–$C_4$ alkyl radical; a hydroxy($C_1$–$C_4$ alkoxy)-$C_1$–$C_4$ alkyl radical; a $C_1$–$C_4$ aminoalkyl radical; a $C_1$–$C_4$ aminoalkyl radical whose amine is mono- or disubstituted by a $C_1$–$C_4$ alkyl radical, by an acetyl radical, by a $C_1$–$C_4$ monohydroxyalkyl radical or by a $C_2$–$C_4$ polyhydroxyalkyl radical; a ($C_1$–$C_4$ alkyl)-$C_1$–$C_4$ thioalkyl radical, a monohydroxy($C_1$–$C_4$ alkyl)-$C_1$–$C_4$ thioalkyl radical; a polyhydroxy($C_2$–$C_4$ alkyl)-$C_1$–$C_4$ alkyl radical; a $C_1$–$C_4$ carboxyalkyl radical; a ($C_1$–$C_4$ alkoxy)-$C_1$–$C_4$ thiocarbonylalkyl radical or a $C_1$–$C_4$ acetylaminoalkyl radical; a $C_1$–$C_4$ cyanoalkyl radical; a $C_1$–$C_4$ trifluoroalkyl radical; a $C_1$–$C_4$ haloalkyl radical; a $C_1$–$C_4$ phosphoalkyl radical, or a $C_1$–$C_4$ sulphoalkyl radical;

$R_2$ and $R_3$, which are identical or different, represent a hydrogen or halogen atom; a group Z; a group —NH—Z; a $C_1$–$C_4$ alkyl radical; a carboxyl radical; a ($C_1$–$C_4$ alkoxy)carbonyl radical or a formyl radical;

$R_4$ and $R_5$, which are identical or different, represent a hydrogen or halogen atom; a group Z; a group —NH—Z; a $C_1$–$C_4$ alkyl radical; a $C_1$–$C_4$ alkoxy radical; an acetylamino radical; a $C_1$–$C_5$ monohydroxyalkyl radical; a $C_2$–$C_4$ polyhydroxyalkyl radical; a ($C_1$–$C_4$ alkoxy)-$C_1$–$C_4$ alkyl radical; a thiophene radical; a furan radical; a phenyl radical; an aralkyl radical in which the alkyl moiety is $C_1$–$C_4$; a phenyl radical or aralkyl radical in which the alkyl moiety is $C_1$–$C_4$, each substituted by a halogen atom, by a $C_1$–$C_4$ alkyl radical, by a trifluoromethyl radical, by a $C_1$–$C_4$ alkoxy radical, by an amino radical or by an amino radical which is mono- or disubstituted by a $C_1$–$C_4$ alkyl radical; a ($C_1$–$C_4$ alkyl)-$C_1$–$C_4$ aminoalkyl radical or a di($C_1$–$C_4$ alkyl)-$C_1$–$C_4$ aminoalkyl radical;

Z is selected from the unsaturated cationic groups of formulae (II) and (III) below and the saturated cationic groups of formula (IV) below:

in which:

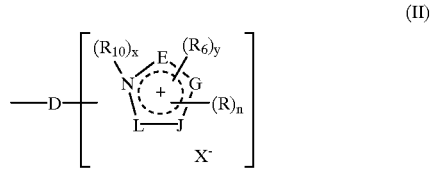

(II)

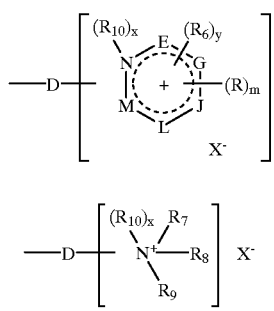

(III)

(IV)

D is a linker which represents an alkyl chain containing preferably 1 to 14 carbon atoms, which is linear or branched and can be interrupted by one or more heteroatoms such as oxygen, sulphur or nitrogen atoms and can be substituted by one or more hydroxyl or $C_1$–$C_6$ alkoxy radicals and can carry one or more ketone functional groups;

the ring members E, G, J, L and M, which are identical or different, represent a carbon, oxygen, sulphur or nitrogen atom;

n is an integer of between 0 and 4 inclusive;

m is an integer of between 0 and 5 inclusive;

the radicals R, which are identical or different, represent a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silyl-$C_1$–$C_6$ alkyl radical, an amido radical, an aldehydo radical, a carboxyl radical, a $C_1$–$C_6$ alkylcarbonyl radical, a thio radical, a $C_1$–$C_6$ thioalkyl radical, a ($C_1$–$C_6$ alkyl)thio radical, an amino radical, an amino radical protected by a ($C_1$–$C_6$ alkyl)carbonyl, carbamyl or ($C_1$–$C_6$ alkyl) sulphonyl radical; a group NHR" or NR"R'" in which R' and R'", which are identical or different, represent a $C_1$–$C_6$ alkyl radical, a $C_1$–$C_6$ monohydroxyalkyl radical or a $C_2$–$C_6$ polyhydroxyalkyl radical;

$R_6$ represents a $C_1$–$C_6$ alkyl radical, a $C_1$–$C_6$ monohydroxyalkyl radical, a $C_2$–$C_6$ polyhydroxyalkyl radical, a $C_1$–$C_6$ cyanoalkyl radical, a tri($C_1$–$C_6$ alkyl)silyl-$C_1$–$C_6$ alkyl radical, a ($C_1$–$C_6$ alkoxy)-$C_1$–$C_6$ alkyl radical, a $C_1$–$C_6$ carbamylalkyl radical, a ($C_1$–$C_6$ alkyl)-$C_1$–$C_6$ carboxyalkyl radical, a benzyl radical or a group Z of formula (II), (III) or (IV) as defined above;

$R_7$, $R_8$ and $R_9$, which are identical or different, represent a $C_1$–$C_6$ alkyl radical, a $C_1$–$C_6$ monohydroxyalkyl radical, a $C_2$–$C_6$ polyhydroxyalkyl radical, a ($C_1$–$C_6$ alkoxy)-$C_1$–$C_6$ alkyl radical, a $C_1$–$C_6$ cyanoalkyl radical, an aryl radical, a benzyl radical, a $C_1$–$C_6$ amidoalkyl radical, a tri($C_1$–$C_6$ alkyl)silyl-$C_1$–$C_6$ alkyl radical or a $C_1$–$C_6$ aminoalkyl radical whose amine is protected by a ($C_1$–$C_6$ alkyl)carbonyl, carbamyl or ($C_1$–$C_6$ alkyl)sulphonyl radical; where two of the radicals $R_7$, $R_8$ and $R_9$ may also form, together with the nitrogen atom to which they are attached, a 5- or 6-membered saturated ring containing carbon or containing at least one additonal heteroatoms, such as, for example, a pyrrolidine ring, a piperidine ring, a piperazine ring or a morpholine ring, it being possible for the said ring to be unsubstituted or substituted by a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silyl-$C_1$–$C_6$ alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$ alkyl)thio radical, an amino radical, or an amino radical protected by a ($C_1$–$C_6$ alkyl)carbonyl, carbamyl or ($C_1$–$C_6$ alkyl)sulphonyl radical; one of the radicals $R_7$, $R_8$ and $R_9$ may also represent a second group Z which is identical to or different from the first group Z;

$R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical or a $C_1$–$C_6$ aminoalkyl radical whose amine is protected by a ($C_1$–$C_6$ alkyl)carbonyl, carbamyl or ($C_1$–$C_6$ alkyl)sulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a tri($C_1$–$C_6$ alkyl)silyl-$C_1$–$C_6$ alkyl radical; a $C_1$–$C_6$ sulphonamidoalkyl radical; a ($C_1$–$C_6$-alkyl)carboxy-$C_1$–$C_6$ alkyl radical; a ($C_1$–$C_6$ alkyl)sulphinyl-$C_1$–$C_6$ alkyl radical; a ($C_1$–$C_6$ alkyl)sulphonyl-$C_1$–$C_6$ alkyl radical; a ($C_1$–$C_6$ alkyl)keto-$C_1$–$C_6$ alkyl radical; an N-($C_1$–$C_6$ alkyl)carbamyl-$C_1$–$C_6$ alkyl radical; or an N-($C_1$–$C_6$ alkyl)sulphonamido-$C_1$–$C_6$ alkyl radical;

x and y are integers equal to 0 or 1; with the following conditions:

in the unsaturated cationic groups of formula (II):
when x is 0, the linker D is attached to the nitrogen atom,
when x is 1, the linker D is attached to one of the ring members E, G, J or L,
y can adopt the value 1 only:
1) when the ring members E, G, J and L represent simultaneously a carbon atom and when the radical $R_6$ is carried by the nitrogen atom of the unsaturated ring; or else
2) when at least one of the ring members E, G, J and L represents a nitrogen atom to which the radical $R_6$ is attached;

in the unsaturated cationic groups of formula (III):
when x is 0, the linker D is attached to the nitrogen atom,
when x is 1, the linker D is attached to one of the ring members E, G, J, L or M,
y can adopt the value 1 only when at least one of the ring members E, G, J, L and M represents a divalent atom and when the radical $R_6$ is carried by the nitrogen atom of the unsaturated ring;

in the cationic groups of formula (IV):
when x is 0, the linker is attached to the nitrogen atom which carries the radicals $R_7$ to $R_9$,
when x is 1, two of the radicals $R_7$ to $R_9$ form, conjointly with the nitrogen atom to which they are attached, a 5- or 6-membered saturated ring as defined above, and the linker D is carried by a carbon atom of the said saturated ring;

$X^-$ represents a monovalent or divalent anion selected preferably from a halogen atom such as chlorine, bromine, fluorine or iodine, a hydroxide, a hydrogen sulphate or a $C_1$–$C_6$-alkyl sulphate such as, for example, a methyl sulphate or an ethyl sulphate;

with the proviso that:

the number of cationic groups Z of formula (II), (III) or (IV) is at least 1.

As indicated above, the colorations obtained with the oxidation dyeing composition in accordance with the invention can be intense and make it possible to obtain shades within a very wide range of colours. Moreover, they can exhibit excellent properties of resistance with respect to the action of various external agents (light, inclement weather, washing, permanent-waving, perspiration, friction). These properties can be particularly remarkable as regards, notably, the resistance of the colorations obtained with respect to the action of light, washing and perspiration.

In the formula (I) above the alkyl and alkoxy radicals can be linear or branched.

Among the rings of the unsaturated groups Z of formula (II) above, mention may be made in particular, by way of example, of pyrrole, imidazole, pyrazole, oxazole, thiazole and triazole rings.

Among the rings of the unsaturated groups Z of formula (III) above, mention may be made, in particular, by way of example, of pyridine, pyrimidine, pyrazine, oxazine and triazine rings.

Among the compounds of formula (I) above, mention may be made in particular of:

3-(4-hydroxy-1-methyl-1H-indol-5-yl methyl)-1-methyl pyridinium methosulphate;

4-(4-hydroxy-1-methyl-1H-indol-5-ylmethyl)-1-methyl pyridinium methosul phate;

3-[3-(4-hydroxy-5-(1-methylpyridinium)-4-ylmethylindol-1-yl )propyl]-1-methylimidazol-1-ium dimethosulphate;

4-(4-hydroxy-1-(2-hydroxyethyl)-1H-indol-5-ylmethyl)-1-methylpyridinium methosulphate;

3-[3-(4-hydroxy-5-(1-methylpyridinium)-5-ylmethyl-indol-1-yl )propyl]-1-methylimidazol-1-ium dimethosulphate;

3-[4-hydroxy-5-(1-methylpyridinium)-3-ylmethyl-indol-1-ylmethyl]-1-methylpyridinium dimethosulphate;

3-[3-(5-benzyl-4-hydroxyindol-1-yl)propyl]-1-methyl-3H-imidazol-1-ium methosulphate;

[2-(4-hydroxy-1H-indol-3-yl)ethyl]trimethyl-ammonium methosulphate;

[2-(4-hydroxy-1-methyl-1H-indol-3-yl)ethyl]-trimethylammonium methosulphate;

(4-hydroxy-1-methyl-1H-indol-3-ylmethyl)-trimethylammonium methosulphate;

(4-hydroxy-1H-indol-3-ylmethyl)trimethylammonium methosulphate;

{3-[(4-hydroxy-1H-indole-2-carbonyl)amino]propyl}-trimethylammonium methosulphate;

{3-[(4-hydroxy-1-methyl-1H-indole-2-carbonyl)-amino] propyl}trimethylammonium methosulphate;

{3-[(4-hydroxy-5-methyl-1H-indole-2-carbonyl)-amino] propyl}trimethylammonium methosulphate;

{3-[(4-hydroxy-1,5-dimethyl-1H-indole-2-carbonyl) amino]propyl}trimethylammonium methosulphate;

3-{3-[(4-hydroxy-1H-indole-2-carbonyl)amino]-propyl}-1-methyl-3H-imidazol-1-ium methosulphate;

3-{3-[(4-hydroxy-1-methyl-1H-indole-2-carbonyl )-amino]propyl}-1-methyl-3H-imidazol-1-ium methosulphate;

3-{3-[(4-hydroxy-5-methyl-1H-indole-2-carbonyl)-amino]propyl}-1-methyl-3H-imidazol-1-ium methosulphate;

3-{3-[(4-hydroxy-1,5-dimethyl-1H-indole-2-carbonyl) amino]propyl}1-methyl-3H-imidazol-1-ium methosulphate;

{3-[(4-hydroxy-1H-indole-6-carbonyl)amino]propyl}-trimethylammonium monochloride;

{3-[(4-hydroxy-1-methyl-1H-indole-6-carbonyl)-amino] propyl}trimethylammonium monochloride;

and their addition salts with an acid.

The compounds of formula (I) in accordance with the invention can be readily obtained in accordance with well-known methods of the prior art such as, for example, in accordance with the preparation process described in the patent application FR-A-2 736 640, the disclosure of which is incorporated by reference herein, followed by a conventional final quaternization step.

The invention additionally provides for the use of the compounds of formula (I) in accordance with the invention as a coupler for the oxidation dyeing of keratinous fibers and, in particular, of human keratinous fibers such as the hair.

The invention also provides a composition for the oxidation dyeing of keratinous fibers and, in particular, of human keratinous fibers such as the hair, characterized in that it comprises, in a medium appropriate for dyeing, at least one compound of formula (I) in accordance with the invention.

The compound or compounds of formula (I) in accordance with the invention and/or its or their addition salt or salts with an acid represents or represent preferably from 0.0005 to 12% by weight, approximately, of the total weight of the dyeing composition, and, more preferably still, from 0.005 to 6% by weight, approximately, of this weight.

In accordance with one preferred embodiment of the invention, the dyeing composition additionally includes one or more oxidation bases which can be selected from the oxidation bases conventionally used in oxidation dyeing and among which mention may be made in particular of para-phenylenediamines, bisphenylalkylenediamines, para-aminophenols, ortho-aminophenols and heterocyclic bases.

Among the para-phenylenediamines, mention may be made more particularly, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N ,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hyd roxyethyloxy-para-phenylenediarnine, 2-β-acetylaminoethyloxy-para-phenylenediamine, N-(β-methoxyethyl)-para-phenylenediamine and their addition salts with an acid.

Among the abovementioned para-phenylenediamines, very particular preference is given to para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)- paraphenylenediamine, 2-chloro-para-phenylenediamine, 2-β-acetylaminoethyloxy-para-phenylenediamine, and their addition salts with an acid.

Among the bisphenylalkylenediamines, mention may be made, more particularly, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylene-diamine, N,N'-bis(4-methylaminophenyl)tetramethylene-diamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among the para-aminophenols, mention may be made more particularly, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2(β-hydroxyethylaminomethyl)phenol, 4-amino-2-fluorophenol, and their addition salts with an acid.

Among the ortho-aminophenols, mention may be made more particularly, by way of example, of 2-aminophenol, 2-amino-5-methylphenol, 2-amino-6-methylphenol, 5-acetamido-2-aminophenol, and their addition salts with an acid.

Among the heterocyclic bases, mention may be made more particularly, by way of example, of pyridine derivatives, pyrimidine derivatives and pyrazole derivatives.

Among the pyridine derivatives, mention may be made more particularly of the compounds described, for example, in the patents GB 1 026 978 and GB 1 153 196, the disclosures of each which are incorporated by reference herein, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, mention may be made more particularly of the compounds described, for example, in the German patent DE 2 359 399 or Japanese patents JP 88-169 571 and JP 91-10659 or patent application WO 96/15765, the disclosures of each which are incorporated by reference herein, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolo-pyrimidine derivatives such as those mentioned in the patent application FR-A-2 750 048, the disclosure of which is incorporated by reference herein, and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3-5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, and their addition salts and their tautomeric forms, when a tautomeric equilibrium exists, and their addition salts with an acid.

Among the pyrazole derivatives, mention may be made more particularly of the compounds described in the patents DE 3 843 892, DE 4 133 957 and patent applications WO 94/08969, WO 94/08970, FR-A-2 733 749 and DE 195 43 988, the disclosures of each which are incorporated by reference herein, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl pyrazole, 4-amino-5-(2'-aminoethyl)amino-1,3-dimethyl pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

When they are used, these oxidation bases represent preferably from 0.0005 to 12% by weight, approximately, of the total weight of the dyeing composition, and still more preferably from 0.005 to 6% by weight, approximately, of this weight.

In addition to the compound or compounds of formula (I) above, the dyeing composition in accordance with the invention may also include at least one additional coupler which can be selected from the couplers used conventionally in oxidation dyeing and among which mention may be made in particular of meta-phenylenediamines meta-aminophenols, meta-diphenols and heterocyclic couplers such as, for example, indole derivatives, indoline derivatives, pyridine derivatives and pyrazolones, and their addition salts with an acid.

These couplers are selected more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and their addition salts with an acid.

When they are present, these couplers represent preferably from 0.0001 to 10% by weight, approximately, of the total weight of the dyeing composition, and still more preferably from 0.005 to 5% by weight, approximately, of this weight.

Generally speaking, the addition salts with an acid which can be used in the context of the dyeing compositions of the invention (compounds of formula (I), oxidation bases and additional couplers) are selected in particular from hydrochlorides, hydrobromides, sulphates, citrates, succinates, tartrates, lactates and acetates.

The medium appropriate for dyeing (or vehicle) generally is water or a mixture of water and at least one organic solvent for solubilizing the compounds which would not be sufficiently soluble in water. By way of organic solvent, mention may be made, for example, of $C_1$–$C_4$ lower alkanols, such as ethanol and isopropanol; glycerol; glycols and glycol ethers, such as 2-butoxyethanol, propylene glycol, propylene glycol monomethyl ether, diethylene glycol monoethyl ether and monomethyl ether, and aromatic alcohols, such as benzyl alcohol or phenoxyethanol, similar products, and mixtures thereof.

The solvents can be present in proportions of preferably between I and 40% inclusive by weight, approximately, relative to the total weight of the dyeing composition, and still more preferably between 5 and 30% inclusive by weight, approximately.

The pH of the dyeing composition according to the invention is generally between 3 and 12 inclusive, approximately, and preferably between 5 and 11 inclusive, approximately. It can be adjusted to the desired value by means of acidifying or basifying agents which are commonly employed in the dyeing of keratinous fibers.

Among the acidifying agents, mention may be made, by way of example, of mineral acids or organic acids such as hydrochloric acid, ortho-phosphoric acid, sulphuric acid, carboxylic acids such as acetic acid, tartaric acid, citric acid and lactic acid, and sulphonic acids.

Among the basifying agents, mention may be made, by way of example, of aqueous ammonia, alkali metal carbonates, alkanolamines such as mono-, di- and triethanolamines and their derivatives, sodium hydroxide or potassium hydroxide, and the compounds of formula (V) below:

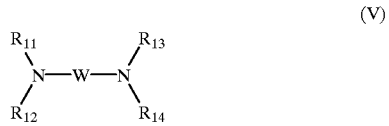

(V)

in which W is a propylene radical optionally substituted by a hydroxyl group or a $C_1$–$C_6$ alkyl radical; and $R_{11}$, $R_{12}$, $R_{13}$ and $R_{14}$, which are identical or different, represent a hydrogen atom or a $C_1$–$C_6$ alkyl or $C_1$–$C_6$ hydroxyalkyl radical.

The oxidation dyeing compositions in accordance with the invention may also include at least one direct dye, in particular for modifying the shades or enriching them with glints.

The dyeing composition in accordance with the invention may also include various adjuvants which are conventionally employed in hair-dyeing compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, penetrants, sequestrants, perfumes, buffers, dispersants, conditioning agents such as, for example, volatile or nonvolatile silicones, modified or otherwise, film formers, ceramides, preservatives and opacifiers.

The person skilled in the art will of course take care to select this or these optional complementary compounds such that the advantageous properties associated intrinsically with the oxidation dyeing composition in accordance with the invention are not, or not substantially, adversely affected by the intended addition or additions.

The dyeing composition according to the invention can be presented in a variety of forms, such as in the form of liquids, creams, gels or any other form appropriate for carrying out dyeing of keratinous fibers and, in particular, of human hair.

The invention also provides a method of oxidation-dyeing keratinous fibers and, in particular, human keratinous fibers such as the hair, employing the dyeing composition as defined above.

In accordance with this method, at least one dyeing composition as defined above is applied to the fibers, the colour being revealed at an acidic, neutral or alkaline pH with the aid of an oxidizing agent which is added to the dyeing composition right at the time of use or which is present in an oxidizing composition which is applied simultaneously or sequentially.

In accordance with a preferred embodiment of the dyeing method of the invention, the above-described dyeing composition is preferably mixed, at the time of use, with an oxidizing composition comprising, in a medium appropriate for dyeing, at least one oxidizing agent which is present in an amount sufficient to develop a coloration. The mixture obtained is subsequently applied to the keratinous fibers and is left to act for from 3 to 50 minutes, approximately, preferably from 5 to 30 minutes, approximately, after which the fibers are rinsed, washed with shampoo, rinsed again and dried.

The oxidizing agent can be selected from the oxidizing agents which are conventionally used for the oxidation dyeing of keratinous fibers, and among which mention may be made of hydrogen peroxide, urea peroxide, alkali metal bromates, persalts such as perborates and persulphates, and enzymes such as peroxidases, laccases and oxidoreductases having 2 electrons. Hydrogen peroxide is particularly preferred.

The pH of the oxidizing composition comprising the oxidizing agent as defined above is such that, after mixing with the dyeing composition, the pH of the resultant composition that is applied to the keratinous fibers varies preferably between 3 and 12 inclusive, approximately, and still more preferably between 5 and 11 inclusive. It is adjusted to the desired value by means of acidifying or basifying agents which are commonly employed in dyeing keratinous fibers, such agents being as defined above.

The oxidizing composition as defined above may also include various adjuvants which are conventionally employed in hair-dyeing compositions, such adjuvants being as defined above.

The composition which is finally applied to the keratinous fibers may be presented in various forms, such as in the form of liquids, creams, gels or any other form appropriate for carrying out dyeing of keratinous fibers and, in particular, of human hair.

The invention also provides a multi-compartment dyeing device or kit, or any other packaging system having two or more compartments, of which a first compartment contains the dyeing composition as defined above and a second compartment contains the oxidizing composition as defined above. These devices can be equipped with a means allowing the desired mixture to be delivered to the hair, such as the devices described in the patent FR-2 586 913, the disclosure of which is incorporated by reference herein, in the name of the applicant.

The examples which follow are intended to illustrate the invention without limiting its scope.

PREPARATION EXAMPLES

Preparation Example 1

Synthesis of 3-(4-hydroxy-1-methyl-1H-indol-5-ylmethyl)-1-methylpyridinium methosulphate

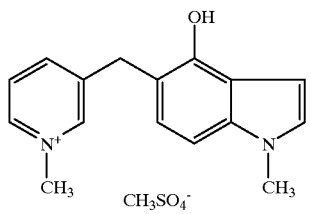

a) Preparation of 1-methyl-5-pyridin-3-ylmethyl-1H-indol-4-ol 500 cm$^3$ of 2-methyl-2-propanol, 75 g of pyridine-3-carboxaldehyde and 100 g of 1-methyl-1,5,6,7-tetrahydroindol-4-one were introduced into a 1-liter reactor equipped with a mechanical stirrer and surmounted by a condenser and a thermometer. After 10 minutes of stirring, 157 g of potassium tert-butoxide were added in small portions over 15 minutes. Following addition, the temperature was held at 75° C. for 1 hour. The reaction mixture was allowed to return to room temperature and then was neutralized (pH=6) with 20% hydrochloric acid. It was poured into 2 kg of ice-water. The precipitate obtained was filtered off with suction and washed with diisopropyl ether and with petroleum ether. It was dried over potash under vacuum at 30° C. This gave 120 g of 1-methyl-5-pyridin-3-ylmethyl-1H-indol-4-ol with a yield of 74%.

b) Preparation of 3-(4-hydroxy-1-methyl-1H-indol-5-ylmethyl)-1-methylpyridinium methosulphate 95 g of 1-methyl-5-pyridin-3-ylmethyl-1H-indol-4-ol in 500 cm$^3$ of ethyl acetate and 53 g of dimethyl sulphate were introduced into a 1-liter reactor equipped with a mechanical stirrer and surmounted by a condenser and a thermometer. This mixture was taken to reflux for 2 hours. The reaction mixture was allowed to return to room temperature and the precipitate was isolated by filtration. The precipitate was subsequently washed with ethyl acetate and with petroleum ether and then dried over potash under vacuum at 30° C.

This gave 140 g of 3-(4-hydroxy-1-methyl-1H-indol-5-ylmethyl)-1-methylpyridinium methosulphate with a yield of 96%. This product was subsequently recrystallized from methanol (2.5 cm$^3$/g); (yield =80%).

The elemental analysis calculated for $C_{16}H_{17}N_2O \cdot CH_3O_4S$ (MW=364.42 g) was:

| % | C | H | N | O | S |
|---|---|---|---|---|---|
| Calculated | 56.03 | 5.53 | 7.69 | 21.95 | 8.80 |
| Found | 56.68 | 5.54 | 7.63 | 21.96 | 8.83 |

APPLICATION EXAMPLES

Examples 1 to 4

Dyeing in an Alkaline Medium

The following dyeing compositions in accordance with the invention were prepared (amounts in grams):

| | EXAMPLE | | | |
|---|---|---|---|---|
| | 1 | 2 | 3 | 4 |
| 3-(4-Hydroxy-1-methyl-1 H-indol-5-ylmethyl)-1-methylpyridinium methosulphate (coupler of formula (I)) | 1.093 | 1.093 | 1.093 | 1.093 |
| para-Aminophenol (oxidation base) | 0.327 | — | — | — |
| 2-β-Acetylaminoethoxy-para-phenylenediamine, 2HCl (oxidation base) | — | 0.798 | — | — |
| 3-Methyl-4-aminophenol (oxidation base) | — | — | 0.369 | — |
| para-Phenylenediamine (oxidation base) | — | — | — | 0.327 |
| Common dyeing vehicle No. 1 | (*) | (*) | (*) | (*) |
| Demineralized water q.s. to | 100 g | 100 g | 100 g | 100 g |

(*) Common dyeing vehicle No. 1:

| | |
|---|---|
| 96° ethyl alcohol | 18 g |
| 35% aqueous sodium metabisulphite solution | 0.68 g |
| Pentasodium salt of diethylenetriaminepentaacetic acid | 1.1 g |
| 20% aqueous ammonia | 10.0 g |

At the time of use, each of the above dyeing compositions were mixed, weight for weight, with a 20-volume (6% by weight) hydrogen peroxide solution with a pH of 3. The mixture obtained was applied to locks of permed grey hair containing 90% white hairs for 30 minutes. The locks were subsequently rinsed, washed with a standard shampoo, rinsed again and then dried.

The shades obtained are given in the table below:

| EXAMPLE | Dyeing pH | Shade obtained |
|---|---|---|
| 1 | 10 ± 0.2 | Iridescent red |
| 2 | 10 ± 0.2 | Blue |
| 3 | 10 ± 0.2 | Iridescent red |
| 4 | 10 ± 0.2 | Dark purplish blue |

What is claimed is:

1. A composition for dyeing keratinous fibers, comprising at least, one coupler chosen from compounds of formula (I) below and the addition salts thereof with an acid:

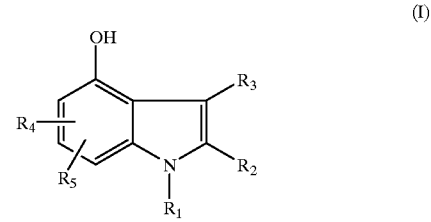

(I)

in which:

$R_1$ is chosen from a hydrogen atom; a group Z; a $C_1$–$C_4$ alkyl radical; a $C_1$–$C_4$ monohydroxyalkyl radical; a $C_2$–$C_4$ polyhydroxyalkyl radical; a ($C_1$–$C_4$ alkoxy)-$C_1$–$C_4$ alkyl radical; a hydroxy($C_1$–$C_4$ alkoxy)-$C_1$–$C_4$ alkyl radical; a $C_1$–$C_4$ aminoalkyl radical; a $C_1$–$C_4$ aminoalkyl radical whose amine is mono- or disubstituted by a $C_1$–$C_4$ alkyl radical, by an acetyl radical, by a $C_1$–$C_4$ monohydroxyalkyl radical or by a $C_2$–$C_4$ polyhydroxyalkyl radical; a ($C_1$–$C_4$ alkyl)-$C_1$–$C_4$ thioalkyl radical, a monohydroxy($C_1$–$C_4$ alkyl)-$C_1$–$C_4$ thioalkyl radical; a polyhydroxy($C_2$–$C_4$ alkyl)-$C_1$–$C_4$ thioalkyl radical; a $C_1$–$C_4$ carboxyalkyl radical; a ($C_1$–$C_4$ alkoxy)-$C_1$–$C_4$ carbonylalkyl radical or a $C_1$–$C_4$ acetylaminoalkyl radical; a $C_1$–$C_4$ cyanoalkyl radical; a $C_1$–$C_4$ trifluoroalkyl radical; a $C_1$–$C_4$ haloalkyl radical; a $C_1$–$C_4$ phosphoalkyl radical, and a $C_1$–$C_4$ sulphoalkyl radical;

$R_2$ and $R_3$, which may be identical or different, are chosen from a hydrogen or halogen atom; a group Z; a group —NH—Z; a $C_1$–$C_4$ alkyl radical; a carboxyl radical; a ($C_1$–$C_4$ alkoxy)carbonyl radical or a formyl radical;

$R_4$ and $R_5$, which may be identical or different, are chosen from a hydrogen or halogen atom; a group Z; a group —NH—Z; a $C_1$–$C_4$ alkyl radical; a $C_1$–$C_4$ alkoxy radical; an acetylamino radical; a $C_1$–$C_5$ monohydroxyalkyl radical; a $C_2$–$C_4$ polyhydroxyalkyl radical; a ($C_1$–$C_4$ alkoxy)-$C_1$–$C_4$ alkyl radical; a thiophene radical; a furan radical; a phenyl radical; an aralkyl radical in which the alkyl moiety is $C_1$–$C_4$; a phenyl radical or aralkyl radical in which the alkyl moiety is $C_1$–$C_4$, each substituted by a halogen atom, by a $C_1$–$C_4$ alkyl radical, by a trifluoromethyl radical, by a $C_1$–$C_4$ alkoxy radical, by an amino radical or by an amino radical which is mono- or disubstituted by a $C_1$–$C_4$ alkyl radical; a ($C_1$–$C_4$ alkyl)-$C_1$–$C_4$ aminoalkyl radical and a di($C_1$–$C_4$ alkyl)-$C_1$–$C_4$ aminoalkyl radical;

Z is chosen from the unsaturated cationic groups of formulae (II) and (III) below and the saturated cationic groups of formula (IV) below:

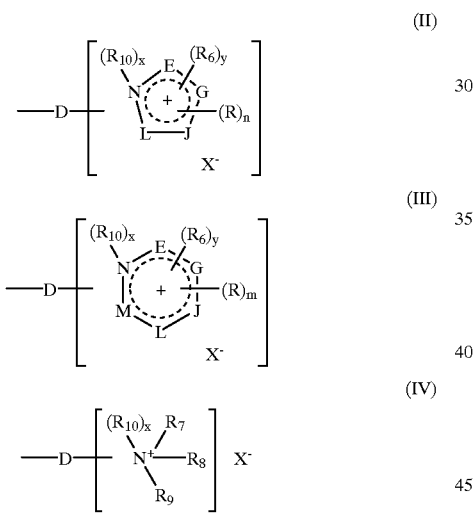

in which:

D is a linker which is an alkyl chain which is linear or branched and can be interrupted by at least one heteroatom and can be substituted by at least one hydroxyl or $C_1$–$C_6$ alkoxy radical and carry at least one ketone functional group;

the ring members E, G, J, L and M, which may be identical or different, are chosen from a carbon, oxygen, sulphur or nitrogen atom;

n is an integer ranging from between 0 and 4 inclusive;

m is an integer ranging from between 0 and 5 inclusive;

the radicals R, which may be identical or different, are chosen from a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silyl-$C_1$–$C_6$ alkyl radical, an amido radical, an aldehydo radical, a carboxyl radical, a $C_1$–$C_6$ alkylcarbonyl radical, a thio radical, a $C_1$–$C_6$ thioalkyl radical, a ($C_1$–$C_6$ alkyl)thio radical, an amino radical, an amino radical protected by a ($C_1$–$C_6$ alkyl)carbonyl, carbamyl or ($C_1$–$C_6$ alkyl)sulphonyl radical; a group NHR" or NR"R"' in which R" and R"', which may be identical or different, are chosen from a $C_1$–$C_6$ alkyl radical, a $C_1$–$C_6$ monohydroxyalkyl radical and a $C_2$–$C_6$ polyhydroxyalkyl radical;

$R_6$ is chosen from a $C_1$–$C_6$ alkyl radical, a $C_1$–$C_6$ monohydroxyalkyl radical, a $C_2$–$C_6$ polyhydroxyalkyl radical, a $C_1$–$C_6$ cyanoalkyl radical, a tri($C_1$–$C_6$ alkyl)silyl-$C_1$–$C_6$ alkyl radical, a ($C_1$–$C_6$ alkoxy)-$C_1$–$C_6$ alkyl radical, a $C_1$–$C_6$ carbamylalkyl radical, a ($C_1$–$C_6$ alkyl)-$C_1$–$C_6$ carboxyalkyl radical, a benzyl radical and a group Z of formula (II), (III) or (IV);

$R_7$, $R_8$ and $R_9$, which may be identical or different, are chosen from a $C_1$–$C_6$ alkyl radical, a $C_1$–$C_6$ monohydroxyalkyl radical, a $C_2$–$C_6$ polyhydroxyalkyl radical, a ($C_1$–$C_6$ alkoxy)-$C_1$–$C_6$ alkyl radical, a $C_1$–$C_6$ cyanoalkyl radical, an aryl radical, a benzyl radica, a $C_1$–$C_6$ amidoalkyl radical, a tri($C_1$–$C_6$ alkyl)silyl-$C_1$–$C_6$ alkyl radical or $C_1$–$C_6$ aminoalkyl radical whose amine is protected by a ($C_1$–$C_6$ alkyl)carbonyl, carbamyl or ($C_1$–$C_6$ alkyl)sulphonyl radical; where two of the radicals $R_7$, $R_8$ and $R_9$ may also form, together with the nitrogen atom to which they are attached, a 5- or 6-membered saturated ring containing carbon or containing at least one heteroatom, it being possible for the said ring to be unsubstituted or substituted by a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silyl-$C_1$–$C_6$ alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$ alkyl)thio radical, an amino radical, or an amino radical protected by a ($C_1$–$C_6$ alkyl)carbonyl, carbamyl or ($C_1$–$C_6$ alkyl)sulphonyl radical;

one of the radicals $R_7$, $R_8$ and $R_9$ may also be chosen from a second group Z which may be identical to or different from the first said group Z;

$R_{10}$ is chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical or a $C_1$–$C_6$ aminoalkyl radical whose amine is protected by a ($C_1$–$C_6$ alkyl)carbonyl, carbamyl or ($C_1$–$C_6$ alkyl)sulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a tri($C_1$–$C_6$ alkyl)silyl-$C_1$–$C_6$ alkyl radical; a $C_1$–$C_6$ sulphonamidoalkyl radical; a ($C_1$–$C_6$-alkyl)carboxy-$C_1$–$C_6$ alkyl radical; a ($C_1$–$C_6$ alkyl)sulphinyl-$C_1$–$C_6$ alkyl radical; a ($C_1$–$C_6$ alkyl)sulphonyl-$C_1$–$C_6$ alkyl radical; a ($C_1$–$C_6$ alkyl)keto-$C_1$–$C_6$ alkyl radical; an N-($C_1$–$C_6$ alkyl)carbamyl-$C_1$–$C_6$ alkyl radical; or an N-($C_1$–$C_6$ alkyl)sulphonamido-$C_1$–$C_6$ alkyl radical x and y are integers equal to 0 or 1; with the following conditions:
in the unsaturated cationic groups of formula (II):
when x is 0, the linker D is attached to the nitrogen atom,
when x is 1, the linker D is attached to one of the ring members E, G, J or L,
y can adopt the value 1 only:

1) when the ring members E, G, J and L are simultaneously a carbon atom and when the radical $R_6$ is carried by the nitrogen atom of the unsaturated ring; or 2) when at least one of the ring members E, G, J and L is a nitrogen atom to which the radical $R_6$ is attached;

in the unsaturated cationic groups of formula (III):
when x is 0, the linker D is attached to the nitrogen atom,
when x is 1, the linker D is attached to one of the ring members E, G, J, L or M,
y can adopt the value 1 only when at least one of the ring members E, G, J, L and M represents a divalent atom and when the radical $R_6$ is carried by the nitrogen atom of the unsaturated ring;

in the cationic groups of formula (IV):
when x is 0, the linker is attached to the nitrogen atom which carries the radicals $R_7$ to $R_9$,
when x is 1, two of the radicals $R_7$ to $R_9$ form, conjointly with the nitrogen atom to which they are attached, a 5- or 6-membered saturated ring as defined above, and the linker D is carried by a carbon atom of the said saturated ring;

$X^-$ is chosen from a monovalent or divalent anion;
with the proviso that:
the number of cationic groups Z of formula (II), (III) or (IV) is at least 1;
wherein the at least one coupler is present in the composition in an amount effective for dyeing keratinous fibers.

2. The composition according to claim 1, wherein said keratinous fibers are human keratinous fibers.

3. The composition according to claim 2, wherein said human keratinous fibers are hair.

4. The composition according to claim 1, wherein said linker D of said group Z is an alkyl chain that comprises 1 to 14 carbon atoms.

5. The composition according to claim 1, wherein said alkyl and alkoxy radicals of said formula (I) are linear or branched.

6. The composition according to claim 1, wherein said at least one heteroatom of said unsaturated cationic groups of formulae (II), (III) and (IV) is chosen from oxygen, sulphur and nitrogen atoms.

7. The composition according to claim 1, wherein said 5- or 6-membered saturated ring containing carbon or containing at least one additional heteroatom formed by two of said radicals $R_7$, $R_8$, and $R_9$ and nitrogen is chosen from a pyrrolidine ring, a piperidine ring, a piperazine ring and a morpholine ring.

8. The composition according to claim 1, wherein said unsaturated groups Z of formula (II) are chosen from pyrrole, imidazole, pyrazole, oxazole, thiazole and triazole rings.

9. The composition according to claim 1, wherein said rings of said unsaturated groups Z of formula (III) are chosen from pyridine, pyrimidine, pyrazine, oxazine and triazine rings.

10. The composition according to claim 1, wherein said $X^-$ is chosen from a halogen atom, a hydroxide, a hydrogen sulphate and a $C_1$–$C_6$ alkyl sulphate.

11. The composition according to claim 1, wherein said at least one coupler is chosen from:

3-(4-hydroxy-1-methyl-1H-indol-5-ylmethyl)-1-methylpyridinium methosulphate;

4-(4-hydroxy-1-methyl-1H-indol-5-ylmethyl)-1-methylpyridinium methosulphate;

3-[3-(4-hydroxy-5-(1-methylpyridinium)-4-ylmethylindol-1-yl)propyl]-1-methylimidazol-1-ium dimethosulphate;

4-(4-hydroxy-1-(2-hydroxyethyl)-1H-indol-5-ylmethyl)-1-methylpyridinium methosulphate;

3-[3-(4-hydroxy-5-(1-methylpyridinium)-5-ylmethyl-indol-1-yl)propyl]-1-methylimidazol-1-ium dimethosulphate;

3-[4-hydroxy-5-(1-methylpyridinium)-3-ylmethyl-indol-1-ylmethyl]-1-methylpyridinium dimethosulphate;

3-[3-(5-benzyl-4-hydroxyindol-1-yl)propyl]-1-methyl-3H-imidazol-1-ium methosulphate;

[2-(4-hydroxy-1H-indol-3-yl)ethyl]trimethyl-ammonium methosulphate;

[2-(4-hydroxy-1-methyl-1H-indol-3-yl)ethyl]-trimethylammonium methosulphate;

(4-hydroxy-1-methyl-1H-indol-3-ylmethyl)-trimethylammonium methosulphate;

(4-hydroxy-1H-indol-3-ylmethyl)trimethylammonium methosulphate;

{3-[(4-hydroxy-1H-indole-2-carbonyl)amino]propyl}-trimethylammonium methosulphate;

{3-[(4-hydroxy-1-methyl-1H-indole-2-carbonyl)-amino]propyl}trimethylammonium methosulphate;

{3-[(4-hydroxy-5-methyl-1H-indole-2-carbonyl)-amino]propyl}trimethylammonium methosulphate;

{3-[(4-hydroxy-1,5-dimethyl-1H-indole-2-carbonyl)amino]propyl}trimethylammonium methosulphate;

3-{3-[(4-hydroxy-1H-indole-2-carbonyl)amino]-propyl}-1-methyl-3H-imidazol-1-ium methosulphate;

3-{3-[(4-hydroxy-1-methyl-1H-indole-2-carbonyl)-amino]propyl}-1-methyl-3H-imidazol-1-ium methosulphate;

3-{3-[(4-hydroxy-5-methyl-1H-indole-2-carbonyl)-amino]propyl}-1-methyl-3H-imidazol-1-ium methosulphate;

3-{3-[(4-hydroxy-1,5-dimethyl-1H-indole-2-carbonyl)amino]propyl}-1-methyl-3H-imidazol-1-ium methosulphate;

{3-[(4-hydroxy-1H-indole-6-carbonyl)amino]propyl}-trimethylammonium monochloride;

{3-[(4-hydroxy-1-methyl-1H-indole-6-carbonyl)-amino]propyl}trimethylammonium monochloride;

and addition salts thereof with an acid.

12. The composition according to claim 1, wherein said addition salts with an acid are chosen from hydrochlorides, hydrobromides, sulphates, citrates, succinates, tartrates, lactates and acetates.

13. The composition according to claim 1, wherein said at least one coupler is present in an amount ranging from 0.0005 to 12% by weight of the total weight of said dyeing composition.

14. The composition according to claim 1, wherein said at least one coupler is present in an amount ranging from 0.005 to 6% by weight of the total weight of said dyeing composition.

15. The composition according to claim 1, wherein said at least one oxidation base is chosen from para-phenylenediamines, bisphenylalkylenediamines, para-aminophenols, ortho-aminophenols and heterocyclic bases.

16. The composition according to claim 15, wherein said para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and the addition salts thereof with an acid.

17. The composition according to claim 15, wherein said para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-paraphenylenediamine, 2-chloro-para-phenylenediamine, 2-β-acetylaminoethyloxy-para-phenylenediamine, and the addition salts thereof with an acid.

18. The composition according to claim 15, wherein said bisphenylalkylenediamines are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)-tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the addition salts thereof with an acid.

19. The composition according to claim 15, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2(β-hydroxyethylamino-methyl)phenol, 4-amino-2-fluorophenol, and the addition salts thereof with an acid.

20. The composition according to claim 15, wherein said ortho-aminophenols are chosen from 2-aminophenol, 2-amino-5-methylphenol, 2-amino-6-methylphenol, 5-acetamido-2-aminophenol, and the addition salts thereof with an acid.

21. The composition according to claim 15, wherein said heterocyclic bases are chosen from pyridine derivatives, pyrimidine derivatives and pyrazole derivatives.

22. The composition according to claim 21, wherein said pyridine derivatives are chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the addition salts thereof with an acid.

23. The composition according to claim 21, wherein said pyrimidine derivatives are chosen from 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolo-pyrimidine derivatives.

24. The composition according to claim 23, wherein said pyrazolo-pyrimidine derivatives are chosen from pyrazolo[1,5-a]pyrimidine-3,7-diamine; 2,5-dimethylpyrazolo[1,5-a]pyrimidine-3,7-diamine; pyrazolo[1,5-a]pyrimidine-3-5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, the addition salts thereof with an acid, and the tautomeric forms thereof when a tautomeric equilibrium exists, and the addition salts thereof with an acid.

25. The composition according to claim 21, wherein said pyrazole derivatives are chosen from 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof with an acid.

26. The composition according to claim 15, wherein said at least one oxidation base is present in an amount ranging from 0.0005 to 12% by weight of the total weight of said dyeing composition.

27. The composition according to claim 15, wherein said at least one oxidation base is present in an amount ranging from 0.005 to 6% by weight of the total weight of said dyeing composition.

28. The composition according to claim 1, wherein said composition further comprises at least one additional coupler that is different from the least one coupler chosen from compounds of formula (I).

29. The composition according to claim 28, wherein said at least one additional coupler is chosen from meta-phenylenediamines, meta-aminophenols, meta-diphenols and heterocyclic couplers.

30. The composition according to claim 28, wherein said at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6- dihydroxy-4-methylpyridine, 1H-3-methylpyrazol-5-one, 1-phenyl-3-methylpyrazol-5-one, and the addition salts thereof with an acid.

31. The composition according to claim 29, wherein said heterocyclic couplers are chosen from indole derivatives, indoline derivatives, pyridine derivatives and pyrazolines, and the addition salts thereof with an acid.

32. The composition according to claim 28, wherein said at least one additional coupler is present in an amount ranging from 0.0001 to 10% by weight, approximately, of the total weight of said dyeing composition.

33. The composition according to claim 28, wherein said at least one additional coupler is present in an amount ranging from 0.005 to 5% by weight, approximately, of the total weight of said dyeing composition.

34. The composition according to claim 28, wherein said addition salts with an acid are chosen from hydrochlorides, hydrobromides, sulphates, citrates, succinates, tartrates, lactates and acetates.

35. The composition according to claim 1, wherein said composition further comprises a medium, wherein said medium comprises water or a mixture of water and at least one organic solvent.

36. The composition according to claim 35, wherein said at least one organic solvent is chosen from $C_1$–$C_4$ lower alkanols; glycerol; glycols and glycol ethers; aromatic alcohols, and mixtures thereof.

37. The composition according to claim 36, wherein said $C_1$–$C_4$ lower alkanols are chosen from ethanol and isopropanol.

38. The composition according to claim 36, wherein said glycols and glycol ethers are chosen from 2-butoxyethanol, propylene glycol, propylene glycol monomethyl ether, diethylene glycol monoethyl ether and monomethyl ether.

39. The composition according to claim 36, wherein said aromatic alcohols are chosen from benzyl alcohol and phenoxyethanol.

40. The composition according to claim 36, wherein said at least one organic solvent is present in an amount ranging from 1 to 40% by weight relative to the total weight of said dyeing composition.

41. The composition according to claim 36, wherein said at least one organic solvent is present in an amount ranging from 5 to 30% by weight relative to the total weight of said dyeing composition.

42. The composition according to claim 1, wherein said composition has a pH ranging from 3 to 12.

43. The composition according to claim 1, wherein said composition has a pH ranging from 5 to 11.

44. The composition according to claim 15, wherein said composition further comprises at least one direct dye.

45. The composition according to claim 15, wherein said at least one oxidation base is present in an amount sufficient for oxidation dyeing.

46. The composition according to claim 15, wherein said composition further comprises at least one oxidizing agent.

47. The composition according to claim 46, wherein said at least one oxidizing agent is chosen from hydrogen peroxide, urea peroxide, alkali metal bromates, persalts, and enzymes.

48. The composition according to claim 47, wherein said persalts are chosen from perborates and persulphates.

49. The composition according to claim 47, wherein said enzymes are chosen from peroxidases, laccases and oxidoreductases having 2 electrons.

50. The composition according to claim 46, wherein said at least one oxidizing agent is a hydrogen peroxide.

51. The composition according to claim 1, wherein said composition is in a form chosen from a liquid, a cream and a gel.

52. A process for dyeing keratin fibers, comprising applying a dyeing composition for the oxidation dyeing of fibers to said fibers and developing for a period of time sufficient to achieve a desired coloration, wherein said dyeing composition comprises:

at least one coupler chosen from compounds of formula (I) below and the addition salts thereof with an acid:

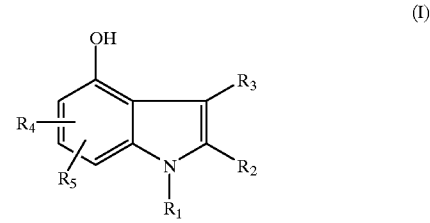

in which:

$R_1$ is chosen from a hydrogen atom; a group Z; a $C_1$–$C_4$ alkyl radical; a $C_1$–$C_4$ monohydroxyalkyl radical; a $C_2$–$C_4$ polyhydroxyalkyl radical; a ($C_1$–$C_4$ alkoxy)-$C_1$–$C_4$ alkyl radical; a hydroxy($C_1$–$C_4$ alkoxy)-$C_1$–$C_4$ alkyl radical; a $C_1$–$C_4$ aminoalkyl radical; a $C_1$–$C_4$ aminoalkyl radical whose amine is mono- or disubstituted by a $C_1$–$C_4$ alkyl radical, by an acetyl radical, by a $C_1$–$C_4$ monohydroxyalkyl radical or by a $C_2$–$C_4$ polyhydroxyalkyl radical; a ($C_1$–$C_4$ alkyl)-$C_1$–$C_4$ thioalkyl radical, a monohydroxy($C_1$–$C_4$ alkyl)-$C_1$–$C_4$ thioalkyl radical; a polyhydroxy($C_2$–$C_4$ alkyl)-$C_1$–$C_4$ thioalkyl radical; a $C_1$–$C_4$ carboxyalkyl radical; a ($C_1$–$C_4$ alkoxy)-$C_1$–$C_4$ carbonylalkyl radical or a $C_1$–$C_4$ acetylaminoalkyl radical; a $C_1$–$C_4$ cyanoalkyl radical; a $C_1$–$C_4$ trifluoroalkyl radical; a $C_1$–$C_4$ haloalkyl radical; a $C_1$–$C_4$ phosphoalkyl radical, and a $C_1$–$C_4$ sulphoalkyl radical;

$R_2$ and $R_3$, which may be identical or different, are chosen from a hydrogen or halogen atom; a group Z; a group —NH—Z; a $C_1$–$C_4$ alkyl radical; a carboxyl radical; a ($C_1$–$C_4$ alkoxy)carbonyl radical or a formyl radical;

$R_4$ and $R_5$, which may be identical or different, are chosen from a hydrogen or halogen atom; a group Z; a group —NH—Z; a $C_1$–$C_4$ alkyl radical; a $C_1$–$C_4$ alkoxy radical; an acetylamino radical; a $C_1$–$C_5$ monohydroxyalkyl radical; a $C_2$–$C_4$ polyhydroxyalkyl radical; a ($C_1$–$C_4$ alkoxy)-$C_1$–$C_4$ alkyl radical; a thiophene radical; a furan radical; a phenyl radical; an aralkyl radical in which the alkyl moiety is $C_1$–$C_4$; a phenyl radical or aralkyl radical in which the alkyl moiety is $C_1$–$C_4$, each substituted by halogen atom, by a $C_1$–$C_4$ alkyl radical, by a trifluoromethyl radical, by a $C_1$–$C_4$ alkoxy radical, by an amino radical or by an amino radical which is mono- or disubstituted by $C_1$–$C_4$ alkyl radical; a ($C_1$–$C_4$ alkyl)-$C_1$–$C_4$ aminoalkyl radical and a di($C_1$–$C_4$ alkyl)-$C_1$–$C_4$ aminoalkyl radical;

Z is chosen from the unsaturated cationic groups of formulae (II) and (III) below and the saturated cationic groups of formula (IV) below:

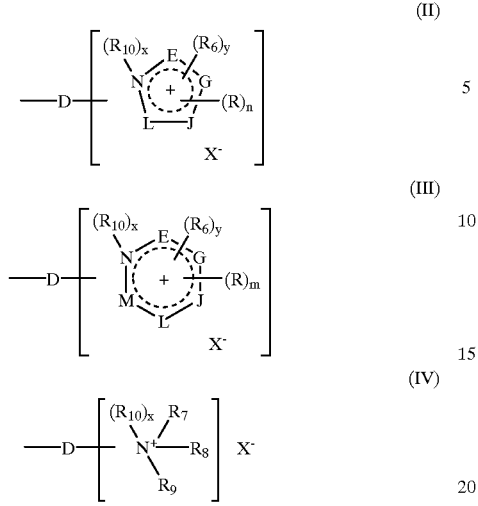

(II)

(III)

(IV)

in which:
- D is a linker which is an alkyl chain which is linear or branched and can be interrupted by at least one heteroatom and can be substituted by at least one hydroxyl or $C_1$–$C_6$ alkoxy radical and carry at least one ketone functional group;
- the ring members E, G, J, L and M, which may be identical or different, are chosen from a carbon, oxygen, sulphur or nitrogen atom;
- n is an integer ranging from between 0 and 4 inclusive;
- m is an integer ranging from between 0 and 5 inclusive;
- the radicals R, which may be identical or different, are chosen from a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silyl-$C_1$–$C_6$ alkyl radical, an amido radical, an aldehydo radical, a carboxyl radical, a $C_1$–$C_6$ alkylcarbonyl radical, a thio radical, a $C_1$–$C_6$ thioalkyl radical, a ($C_1$–$C_6$ alkyl)thio radical, an amino radical, an amino radical protected by a ($C_1$–$C_6$ alkyl)carbonyl, carbamyl or ($C_1$–$C_6$ alkyl) sulphonyl radical; a group NHR" or NR"R'" in which R" and R'", which may be identical or different, are chosen from a $C_1$–$C_6$ alkyl radical, a $C_1$–$C_6$ monohydroxyalkyl radical and a $C_2$–$C_6$ polyhydroxyalkyl radical;
- $R_6$ is chosen from a $C_1$–$C_6$ alkyl radical, a $C_1$–$C_6$ monohydroxyalkyl radical, a $C_2$–$C_6$ polyhydroxyalkyl radical, a $C_1$–$C_6$ cyanoalkyl radical, a tri($C_1$–$C_6$ alkyl) silyl-$C_1$–$C_6$ alkyl radical, a ($C_1$–$C_6$ alkoxy)-$C_1$–$C_6$ alkyl radical, a $C_1$–$C_6$ carbamylalkyl radical, a ($C_1$–$C_6$ alkyl)-$C_1$–$C_6$ carboxyalkyl radical, a benzyl radical and a group Z of formula (II), (III) or (IV);
- $R_7$, $R_8$ and $R_9$, which may be identical or different, are chosen from a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy)-$C_1$–$C_6$ alkyl radical, a $C_1$–C6 cyanoalkyl radical, an aryl radical, a benzyl radical, a $C_1$–$C_6$ amidoalkyl radical, a tri($C_1$–$C_6$ alkyl)silyl-$C_1$–$C_6$ alkyl radical or a $C_1$–$C_6$ aminoalkyl radical whose amine is protected by a ($C_1$–$C_6$ alkyl)carbonyl, carbamyl or ($C_1$–$C_6$ alkyl)sulphonyl radical; where two of the radicals $R_7$, $R_8$ and $R_9$ may also form, together with the nitrogen atom to which they are attached, a 5- or 6-membered saturated ring containing carbon or containing at least one heteroatom, it being possible for the said ring to be unsubstituted or substituted by a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–C6 alkoxy radical, a tri($C_1$–$C_6$ alkyl)silyl-$C_1$–$C_6$ alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$ alkyl)thio radical, an amino radical, or an amino radical protected by a ($C_1$–$C_6$ alkyl)carbonyl, carbamyl or ($C_1$–$C_6$ alkyl)sulphonyl radical;
- one of the radicals $R_7$, $R_8$ and $R_9$ may also be chosen from a second group Z which may be identical to or different from the first said group Z;
- $R_{10}$ is chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical or a $C_1$–$C_6$ aminoalkyl radical whose amine is protected by a ($C_1$–$C_6$ alkyl)carbonyl, carbamyl or ($C_1$–$C_6$ alkyl)sulphonyl radical; a $C_1$–$C_6$ carboxyalkyl radical; a $C_1$–$C_6$ cyanoalkyl radical; a $C_1$–C6 carbamylalkyl radical; a $C_1$–$C_6$ trifluoroalkyl radical; a tri($C_1$–$C_6$ alkyl)silyl-$C_1$–$C_6$ alkyl radical; a $C_1$–$C_6$ sulphonamidoalkyl radical; a ($C_1$–$C_6$-alkyl) carboxy-$C_1$–$C_6$ alkyl radical; a ($C_1$–$C_6$ alkyl)sulphinyl-$C_1$–$C_6$ alkyl radical; a ($C_1$–$C_6$ alkyl)sulphonyl-$C_1$–$C_6$ alkyl radical; a ($C_1$–$C_6$ alkyl)keto-$C_1$–$C_6$ alkyl radical; an N-($C_1$–$C_6$ alkyl)carbamyl-$C_1$–$C_6$ alkyl radical; or an N-($C_1$–$C_6$ alkyl)sulphonamido-$C_1$–$C_6$ alkyl radical;
- x and y are integers equal to 0 or 1; with the following conditions:
  - in the unsaturated cationic groups of formula (II):
    - when x is 0, the linker D is attached to the nitrogen atom,
    - when x is 1, the linker D is attached to one of the ring members E, G, J or L,
    - y can adopt the value 1 only:
      1) when the ring members E, G, J and L are simultaneously a carbon atom and when the radical $R_6$ is carried by the nitrogen atom of the unsaturated ring; or
      2) when at least one of the ring members E, G, J and L is a nitrogen atom to which the radical $R_6$ is attached;
  - in the unsaturated cationic groups of formula (III):
    - when x is 0, the linker D is attached to the nitrogen atom,
    - when x is 1, the linker D is attached to one of the ring members E, G, J, L or M,
    - y can adopt the value 1 only when at least one of the ring members E, G, J, L and M represents a divalent atom and when the radical $R_6$ is carried by the nitrogen atom of the unsaturated ring;
  - in the cationic groups of formula (IV):
    - when x is 0, the linker is attached to the nitrogen atom which carries the radicals $R_7$ to $R_9$,
    - when x is 1, two of the radicals $R_7$ to $R_9$ form, conjointly with the nitrogen atom to which they are attached, a 5- or 6-membered saturated ring as defined above, and the linker D is carried by a carbon atom of the said saturated ring;
- $X^-$ is chosen from a monovalent or divalent anion; with the proviso that:

the number of cationic groups Z of formula (II), (III) or (IV) is at least 1.

53. The process for dyeing keratin fibers according to claim 52, comprising applying said dyeing composition to said fibers, wherein an oxidizing agent is added to said dyeing composition at the time of application.

54. The process for dyeing keratin fibers according to claim 52, comprising applying said dyeing composition to said fibers, wherein an oxidizing agent is present in an oxidizing composition and said oxidizing composition is applied simultaneously or sequentially with said dyeing composition.

55. The process for dyeing keratin fibers according to claim 52, further comprising rinsing said fibers, washing said fibers with shampoo, a second rinsing of said fibers and drying of said fibers.

56. A multi-compartment dyeing kit, comprising at least two separate compartments, wherein a first compartment contains a first compartment and a second compartment contains a second composition, wherein said first composition comprises at least one coupler chosen from compounds of formula (I) below and the addition salts thereof with an acid:

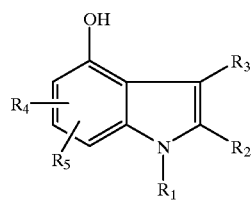

(I)

in which:

R$_1$ is chosen from a hydrogen atom; a group Z; a C$_1$–C$_4$ alkyl radical; a C$_1$–C$_4$ monohydroxyalkyl radical; a C$_2$–C$_4$ polyhydroxyalkyl radical; a (C$_1$–C$_4$ alkoxy)-C$_1$–C$_4$ alkyl radical; a hydroxy(C$_1$–C$_4$ alkoxy)-C$_1$–C$_4$ alkyl radical; a C$_1$–C$_4$ aminoalkyl radical; a C$_1$–C$_4$ aminoalkyl radical whose amine is mono- or disubstituted by a C$_1$–C$_4$ alkyl radical, by an acetyl radical, by a C$_1$–C$_4$ monohydroxyalkyl radical or by a C$_2$–C$_4$ polyhydroxyalkyl radical; a (C$_1$–C$_4$ alkyl)-C$_1$–C$_4$ thioalkyl radical, a monohydroxy(C$_1$–C$_4$ alkyl)-C$_1$–C$_4$ thioalkyl radical; a polyhydroxy(C$_2$–C$_4$ alkyl)-C$_1$–C$_4$ thioalkyl radical; a C$_1$–C$_4$ carboxyalkyl radical; a (C$_1$–C$_4$ alkoxy)-C$_1$–C$_4$ carbonylalkyl radical; a C$_1$–C$_4$ acetylaminoalkyl radical; a C$_1$–C$_4$ cyanoalkyl radical; a C$_1$–C$_4$ trifluoroalkyl radical; a C$_1$–C$_4$ haloalkyl radical; a C$_1$–C$_4$ phosphoalkyl radical, and a C$_1$–C$_4$ sulphoalkyl radical;

R$_2$ and R$_3$, which may be identical or different, are chosen from a hydrogen or halogen atom; a group Z; a group —NH—Z; a C$_1$–C$_4$ alkyl radical; a carboxyl radical; a (C$_1$–C$_4$ alkoxy)carbonyl radical or a formyl radical;

R$_4$ and R$_5$, which may be identical or different, are chosen from a hydrogen or halogen atom; a group Z; a group —NH—Z; a C$_1$–C$_4$ alkyl radical; a C$_1$–C$_4$ alkoxy radical; an acetylamino radical; a C$_1$–C$_5$ monohydroxyalkyl radical; a C$_2$–C$_4$ polyhydroxyalkyl radical; a (C$_1$–C$_4$ alkoxy)-C$_1$–C$_4$ alkyl radical; a thiophene radical; a furan radical; a phenyl radical; an aralkyl radical in which the alkyl moiety is C$_1$–C$_4$; a phenyl radical or aralkyl radical in which the alkyl moiety is C$_1$–C$_4$, each substituted by a halogen atom, by a C$_1$–C$_4$ alkyl radical, by a trifluoromethyl radical, by a C$_1$–C$_4$ alkoxy radical, by an amino radical or by an amino radical which is mono- or disubstituted by a C$_1$–C$_4$ alkyl radical; a (C$_1$–C$_4$ alkyl)-C$_1$–C$_4$ aminoalkyl radical and a di(C$_1$–C$_4$ alkyl)-C$_1$–C$_4$ aminoalkyl radical; Z is chosen from the unsaturated cationic groups of formulae (II) and (III) below and the saturated cationic groups of formula (IV) below:

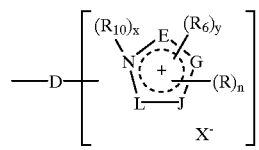

(II)

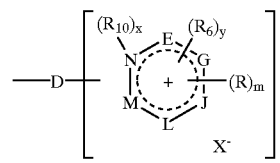

(III)

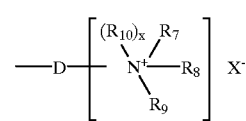

(IV)

in which:

D is a linker which is an alkyl chain which is linear or branched and can be interrupted by at least one heteroatom and can be substituted by at least one hydroxyl or C$_1$–C$_6$ alkoxy radical and carry at least one ketone functional group;

the ring members E, G, J, L and M, which may be identical or different, are chosen from a carbon, oxygen, sulphur or nitrogen atom;

n is an integer ranging from between 0 and 4 inclusive;

m is an integer ranging from between 0 and 5 inclusive;

the radicals R, which may be identical or different, are chosen from a group Z, a halogen atom, a hydroxyl radical, a C$_1$–C$_6$ alkyl radical, a C$_1$–C$_6$ monohydroxyalkyl radical, a C$_2$–C$_6$ polyhydroxyalkyl radical, a nitro radical, a cyano radical, a C$_1$–C$_6$ cyanoalkyl radical, a C$_1$–C$_6$ alkoxy radical, a tri(C$_1$–C$_6$ alkyl)silyl-C$_1$–C$_6$ alkyl radical, an amido radical, an aldehydo radical, a carboxyl radical, a C$_1$–C$_6$ alkylcarbonyl radical, a thio radical, a C$_1$–C$_6$ thioalkyl radical, a (C$_1$–C$_6$ alkyl)thio radical, an amino radical, an amino radical protected by a (C$_1$–C$_6$ alkyl)carbonyl, carbamyl or (C$_1$–C$_6$ alkyl) sulphonyl radical; a group NHR" or NR"R'" in which R" and R'", which may be identical or different, are chosen from a C$_1$–C$_6$ alkyl radical, a C$_1$–C$_6$ monohydroxyalkyl radical and a C$_2$–C$_6$ polyhydroxyalkyl radical;

R$_6$ is chosen from a C$_1$–C$_6$ alkyl radical, a C$_1$–C$_6$ monohydroxyalkyl radical, a C$_2$–C$_6$ polyhydroxyalkyl radical, a C$_1$–C$_6$ cyanoalkyl radical, a tri(C$_1$–C$_6$ alkyl) silyl-C$_1$–C$_6$ alkyl radical, a (C$_1$–C$_6$ alkoxy)-C$_1$–C$_6$ alkyl radical, a C$_1$–C$_6$ carbamylalkyl radical, a (C$_1$–C$_6$ alkyl)-C$_1$–C$_6$ carboxyalkyl radical, a benzyl radical and a group Z of formula (II), (III) or (IV);

R$_7$, R$_8$ and R$_9$, which may be identical or different, are chosen from a C$_1$–C$_6$ alkyl radical, a C$_1$–C$_6$ monohydroxyalkyl radical, a C$_2$–C$_6$ polyhydroxyalkyl radical, a ($C_1$–$C_6$ alkoxy)-$C_1$–$C_6$ alkyl radical, a $C_1$–$C_6$ cyanoalkyl radical, an aryl radical, a benzyl radical, a $C_1$–$C_6$ amidoalkyl radical, a tri($C_1$–$C_6$ alkyl)silyl-$C_1$–$C_6$ alkyl radical or a $C_1$–$C_6$ aminoalkyl radical whose amine is protected by a ($C_1$–$C_6$ alkyl)carbonyl, carbamyl or ($C_1$–$C_6$ alkyl)sulphonyl radical; where two of the radicals $R_7$, $R_8$ and $R_9$ may also form, together with the nitrogen atom to which they are attached, a 5- or 6-membered saturated ring containing carbon or containing at least one additional heteroatom, it being possible for the said ring to be unsubstituted or substituted by a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a $C_1$–$C_6$ cyanoalkyl radical, a $C_1$–$C_6$ alkoxy radical, a tri($C_1$–$C_6$ alkyl)silyl-$C_1$–$C_6$ alkyl radical, an amido radical, an aldehydo radical, a carboxyl radical, a $C_1$–$C_6$ ketoalkyl radical, a thio radical, a $C_1$–$C_6$ thioalkyl radical, a ($C_1$–$C_6$ alkyl)thio radical, an amino radical, or an amino radical protected by a ($C_1$–$C_6$ alkyl)carbonyl, carbamyl or ($C_1$–$C_6$ alkyl) sulphonyl radical; one of the radicals $R_7$, $R_8$ and $R_9$ may also be chosen from a second group Z which may be identical to or different from the first said group Z;

$R_{10}$ is chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical or a $C_1$–$C_6$ aminoalkyl radical whose amine is protected by a ($C_1$–$C_6$ alkyl)carbonyl, carbamyl or ($C_1$–$C_6$ alkyl)sulphonyl radical; a $C_1$–$C_6$ carboxyalkyl radical; a $C_1$–$C_6$ cyanoalkyl radical; a $C_1$–$C_6$ carbamylalkyl radical; a $C_1$–$C_6$ trifluoroalkyl radical; a tri($C_1$–$C_6$ alkyl)silyl-$C_1$–$C_6$ alkyl radical; a $C_1$–$C_6$ sulphonamidoalkyl radical; a ($C_1$–$C_6$-alkyl)carboxy-$C_1$–$C_6$ alkyl radical; a ($C_1$–$C_6$ alkyl)sulphinyl-$C_1$–$C_6$ alkyl radical; a ($C_1$–$C_6$ alkyl)sulphonyl-$C_1$–$C_6$ alkyl radical; a ($C_1$–$C_6$ alkyl)keto-$C_1$–$C_6$ alkyl radical; an N-($C_1$–$C_6$ alkyl)carbamyl-$C_1$–$C_6$ alkyl radical; or an N-($C_1$–$C_6$ alkyl)sulphonamido-$C_1$–$C_6$ alkyl radical;

x and y are integers equal to 0 or 1; with the following conditions:
  in the unsaturated cationic groups of formula (II):
    when x is 0, the linker D is attached to the nitrogen atom,
    when x is 1, the linker D is attached to one of the ring members E, G, J or L,
    y can adopt the value 1 only:
      1) when the ring members E, G, J and L are simultaneously a carbon atom and when the radical $R_6$ is carried by the nitrogen atom of the unsaturated ring; or
      2) when at least one of the ring members E, G, J and L is a nitrogen atom to which the radical $R_6$ is attached;
  in the unsaturated cationic groups of formula (III):
    when x is 0, the linker D is attached to the nitrogen atom,
    when x is 1, the linker D is attached to one of the ring members E, G, J, L or M,
    y can adopt the value 1 only when at least one of the ring members E, G, J, L and M represents a divalent atom and when the radical $R_6$ is carried by the nitrogen atom of the unsaturated ring;
  in the cationic groups of formula (IV):
    when x is 0, the linker is attached to the nitrogen atom which carries the radicals $R_7$ to $R_9$,
    when x is 1, two of the radicals $R_7$ to $R_9$ form, conjointly with the nitrogen atom to which they are attached, a 5- or 6-membered saturated ring as defined above, and the linker D is carried by a carbon atom of the said saturated ring;

$X^-$ is chosen from a monovalent or divalent anion; with the proviso that:
  the number of cationic groups Z of formula (II), (III) or (IV) is at least 1, and
  wherein said second composition comprises at least one oxidizing agent.

* * * * *

UNITED STATES PATENT AND TRADEMARK OFFICE
CERTIFICATE OF CORRECTION

PATENT NO. : 6,306,181 B1
DATED : October 23, 2001
INVENTOR(S) : Eric Terranova et al.

It is certified that error appears in the above-identified patent and that said Letters Patent is hereby corrected as shown below:

Column 12,
Line 40, after "at least", delete "," and insert -- one oxidation base and at least --.

Column 14,
Line 20, "benzyl radica" should read -- benzyl radical --.
Line 22, before "$C_1$-$C_6$ aminoalkyl", insert -- a --.
Line 59, after "radical", insert -- ; --.

Column 18,
Line 52, before "least one", insert -- at --.

Column 20,
Line 58, before "halogen atom", insert -- a --.
Line 61, before "$C_1$-$C_4$ alkyl", insert -- a --.

Column 21,
Line 61, "($C_1$-$C_6$ alkoxy)-$C_1$-$C_6$" should read -- ($C_1$-$C_6$ alkoxy)-$C_1$-$C_6$ --; and "$C_1$-C6" should read -- $C_1$-$C_6$ --.

Column 22,
Line 8, "$C_1$C6 alkoxy" should read -- $C_1$-$C_6$ alkoxy --.

Column 23,
Line 18, "contains a first compartment" should read -- contains a first composition --.

Column 52,
Line 26, "$C_1$-C6 carbamylalkyl" should read -- $C_1$-$C_6$ carbamylalkyl --.

Signed and Sealed this

Fifth Day of August, 2003

JAMES E. ROGAN
*Director of the United States Patent and Trademark Office*